(12) United States Patent
Handal-Orefice

(10) Patent No.: US 11,166,966 B2
(45) Date of Patent: Nov. 9, 2021

(54) COMPOUNDS FOR PRENATAL TREATMENT COMPRISING A NATAL VITAMIN AND ASPIRIN AND METHODS FOR MAKING AND USING THE SAME

(71) Applicant: Roxane Handal-Orefice, New York, NY (US)

(72) Inventor: Roxane Handal-Orefice, New York, NY (US)

( * ) Notice: Subject to any disclaimer, the term of this patent is extended or adjusted under 35 U.S.C. 154(b) by 213 days.

(21) Appl. No.: 15/802,542

(22) Filed: Nov. 3, 2017

(65) Prior Publication Data
US 2019/0134065 A1    May 9, 2019

(51) Int. Cl.
| | |
|---|---|
| *A61K 31/616* | (2006.01) |
| *A61K 9/50* | (2006.01) |
| *A23L 33/00* | (2016.01) |
| *A23L 33/15* | (2016.01) |
| *A23L 33/16* | (2016.01) |
| *A23L 33/10* | (2016.01) |
| *A23L 33/155* | (2016.01) |
| *A61K 9/28* | (2006.01) |
| *A23L 33/12* | (2016.01) |

(52) U.S. Cl.
CPC .......... *A61K 31/616* (2013.01); *A23L 33/10* (2016.08); *A23L 33/12* (2016.08); *A23L 33/15* (2016.08); *A23L 33/155* (2016.08); *A23L 33/16* (2016.08); *A23L 33/30* (2016.08); *A61K 9/2846* (2013.01); *A61K 9/50* (2013.01); *A23V 2002/00* (2013.01)

(58) Field of Classification Search
CPC ...... A61K 31/616; A61K 9/2846; A61K 9/50; A23L 33/10; A23L 33/12; A23L 33/30; A23L 33/16; A23L 33/15; A23L 33/155; A23V 2002/00
See application file for complete search history.

(56) References Cited

U.S. PATENT DOCUMENTS

2005/0187144 A1 * 8/2005 Fine .................... A61K 31/155
514/593

FOREIGN PATENT DOCUMENTS

EP      0947198    * 10/1999

OTHER PUBLICATIONS

One a Day (Women's Prenatal 1 Multivitamins, 20 count, Amazon, Sale date: Apr. 6, 2015).*
WebMD (Aspirin Advised for Some Pregnant Women, Apr. 7, 2014).*
The America College of Obstetricians and Gynecologists, Identification and referral of maternal genetic conditions in pregnancy, Committee Opinion No. 643, 126, e49-51, Oct. 2015.*
Healthy Pets, Aspirin Powder by VEDCO, published online: May 9, 2016. (Year: 2016).*
Blackburn Distributions, Folic Acid Powder, copyright: 2021. (Year: 2021).*

* cited by examiner

*Primary Examiner* — Genevieve S Alley
(74) *Attorney, Agent, or Firm* — K&L Gates LLP

(57) ABSTRACT

Compounds including vitamins and aspirin are disclosed. The compounds are provided in dosage form and preferably include selected amounts of folic acid, vitamin D, calcium, vitamin C, thiamine, and riboflavin with the aspirin. A protective coating is preferably provided between the aspirin and the other vitamin and mineral constituents. The dosages are effective in the treatment and prevention of pre-natal conditions.

6 Claims, 3 Drawing Sheets

COMPOUNDS FOR PRENATAL TREATMENT COMPRISING A NATAL VITAMIN AND ASPIRIN AND METHODS FOR MAKING AND USING THE SAME

BACKGROUND

During or after pregnancy, a woman may be subject to a number of ailments, including pre-eclampsia, pulmonary embolisms, preterm labor or other such ailments, as well as being at risk for a premature delivery of the fetus. A number of studies have shown that taking aspirin during pregnancy may reduce or eliminate these conditions. Pregnant women may not, however, take aspirin at all or may not take it in ideal dosages or at regular intervals to thereby maximize its efficacy. Currently aspirin alone is recommended in high risk women who are pregnant, but often patients are not compliant to this recommendation due to the number of other medications they have to take for other co-existing conditions.

A need exists, therefore, for system and method to enable and encourage pregnant women to take aspirin during pregnancy and to provide a guide to dosage amount and adherence.

BRIEF DESCRIPTION OF THE DRAWINGS

For a more complete understanding of the present disclosure, reference is now made to the following description taken in conjunction with the accompanying drawings.

DETAILED DESCRIPTION

Figure 1:
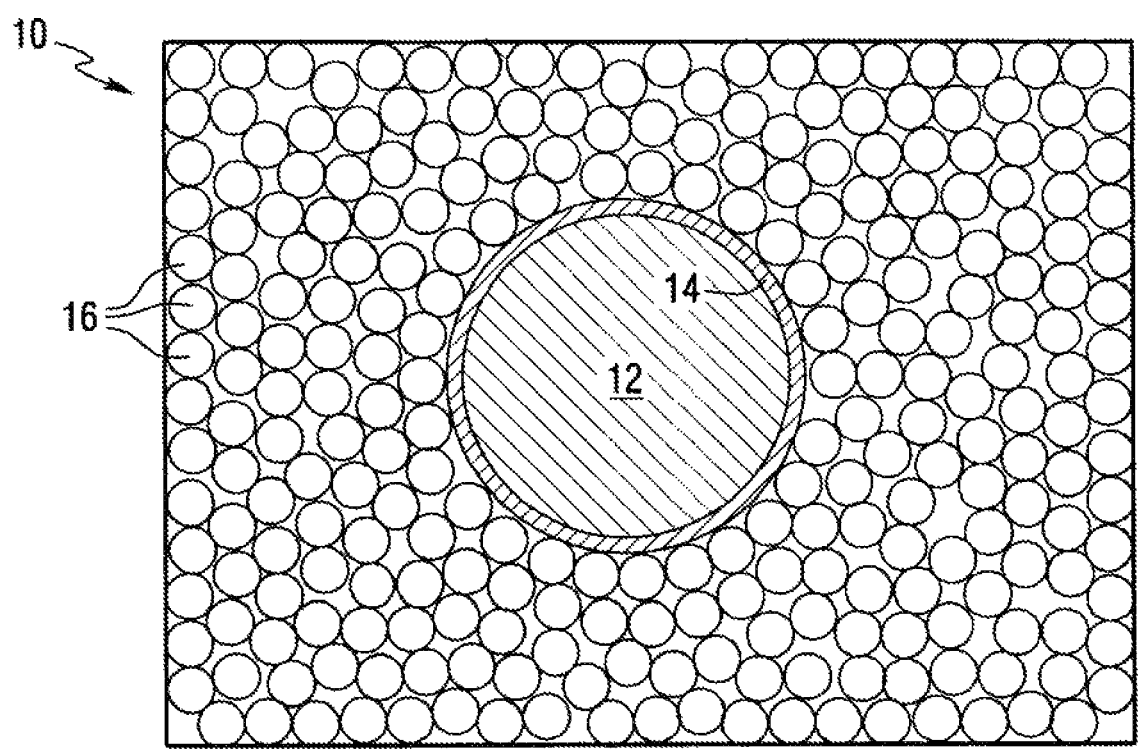
FIG. 1 is an illustration of a prenatal vitamin and aspirin compound dosage according to embodiments of the present disclosure.

The compounds of the present disclosure include a combination of vitamins and aspirin (i.e., acetylsalicylic acid) in effective amounts for the treatment of prenatal patients. The prenatal vitamin component of the compound preferably includes one or more of folic acid, vitamin D, calcium, vitamin C, thiamine, riboflavin, niacin, vitamin B12, vitamin E, zinc, iron, omega 3 DHA, DHC, and/or iodine. One or more of these ingredients may be combined with aspirin in a dosage form which is effective for the treatment of prenatal diseases or ailments, such as but not limited to pre-eclampsia, pulmonary embolisms, or premature delivery. By combining a prenatal vitamin with a dose of aspirin, pregnant women can receive the benefits of taking aspirin while pregnant without the need for managing another pill or dosage, thereby improving adherence.

The dosage of folic acid preferably includes from about 200 to about 600 micrograms (mcg) of the dosage; more preferably, from about 300 to about 500 micrograms. In some embodiments, the dosage of folic acid is about 400 mcg. Folic acid may act as a coenzyme in DNA and RNA synthesis and is may be important for protein metabolism. The action of the folic acid may be enhanced when vitamin B12, vitamin C, and/or zinc are present.

The dosage of vitamin D preferably includes from about 200 to about 600 international units (IU) of the dosage; more preferably, from about 300 to about 500 IU. In some embodiments, the dosage of vitamin D is about 400 mg, but can range between 200 mg to 600 mg.

The dosage of calcium preferably includes from about 100 to about 400 milligrams (mg) of calcium; more preferably, from about 200 to about 300 mg. In some embodiments, the dosage of calcium is about 250 mg.

The dosage of vitamin C preferably includes from about 40 to about 100 mg of calcium; more preferably, from about 60 to about 80 mg. In some embodiments, the dosage of vitamin C is about 70 mg.

The dosage of thiamine preferably includes from about 1 to about 5 mg of thiamine; more preferably, from about 2 to about 4 mg. In some embodiments, the dosage of thiamine is about 3 mg.

The dosage of riboflavin preferably includes from about 0.5 to about 3.5 mg of riboflavin; more preferably, from about 1 to about 3 mg. In some embodiments, the dosage of riboflavin is about 2 mg.

The dosage of niacin preferably includes from about 10 to about 30 mg of niacin; more preferably, from about 15 to about 25 mg. In some embodiments, the dosage of niacin is about 20 mg.

The dosage of vitamin B12 preferably includes from about 2 to about 10 mcg of vitamin B12; more preferably, from about 4 to about 8 mcg. In some embodiments, the dosage of vitamin B12 is about 6 mcg.

The dosage of vitamin E preferably includes from about 6 to about 14 mg of vitamin E; more preferably, from about 8 to about 12 mg. In some embodiments, the dosage of vitamin E is about 10 mg.

The dosage of zinc preferably includes from about 10 to about 20 mg of zinc; more preferably, from about 13 to about 17 mg. In some embodiments, the dosage of zinc is about 15 mg.

The dosage of iron preferably includes from about 13 to about 21 mg of iron; more preferably, from about 15 to about 19 mg. In some embodiments, the dosage of iron is about 17 mg.

The dosage of iodine preferably includes from about 100 to about 200 mcg of iodine; more preferably, from about 125 to about 175 mcg. In some embodiments, the dosage of iodine is about 150 mcg.

The dosage of aspirin preferably includes from about 60 to about 150 mg of aspirin; more preferably, from about 70 to about 90 mg. In some embodiments, the dosage of aspirin is about 81 mg.

In accordance with embodiments of the present disclosure, the vitamin/aspirin compound is provided in a stable dosage form in which unwanted interaction between the aspirin and the other ingredients is substantially prevented. This stabilization is achieved by providing a protective coating between the aspirin and the natal vitamins. For example, a protective coating may be provided around the aspirin which minimizes or prevents deleterious reactions with the other vitamin and mineral ingredients. The protective coating preferably comprises at least one layer of wax, shellac, hydroxypropyl, methylcellulose phthalate, polyvinyl acetate phthalate and/or cellulose acetate phthalate. In a preferred embodiment, the protective coating comprises an enteric coating which may be applied to tablet formulations or to drug particles or granules used in the subsequent fabrication of capsules. The coatings are applied in single or multiple stages depending upon the desired effect. The coating systems can be either aqueous based or organic solvent based to resist breakdown in the low pH environment of the stomach.

FIG. 1 schematically illustrates a prenatal vitamin and aspirin compound dosage 10 in accordance with an embodiment of the present invention. The dosage 10 may be provided in capsule form, or in any other suitable form. The dosage 10 includes an aspirin unit 12 having a protective coating 14. The aspirin unit 12 is preferably provided in tablet form with an enteric protective coating 14. However, the aspirin unit 12 may be provided in other forms such as a capsule, caplet, or microencapsulated pellets.

The dosage 10 includes vitamin and mineral constituents 16 in the preferred amounts listed previously. In the embodiment shown in FIG. 1, the vitamin and mineral constituents 16 are provided in loose powder form. However, the vitamin and mineral constituents 16 may be provided in other forms such as bilayer form, colloidal form or the like.

Figure 2:
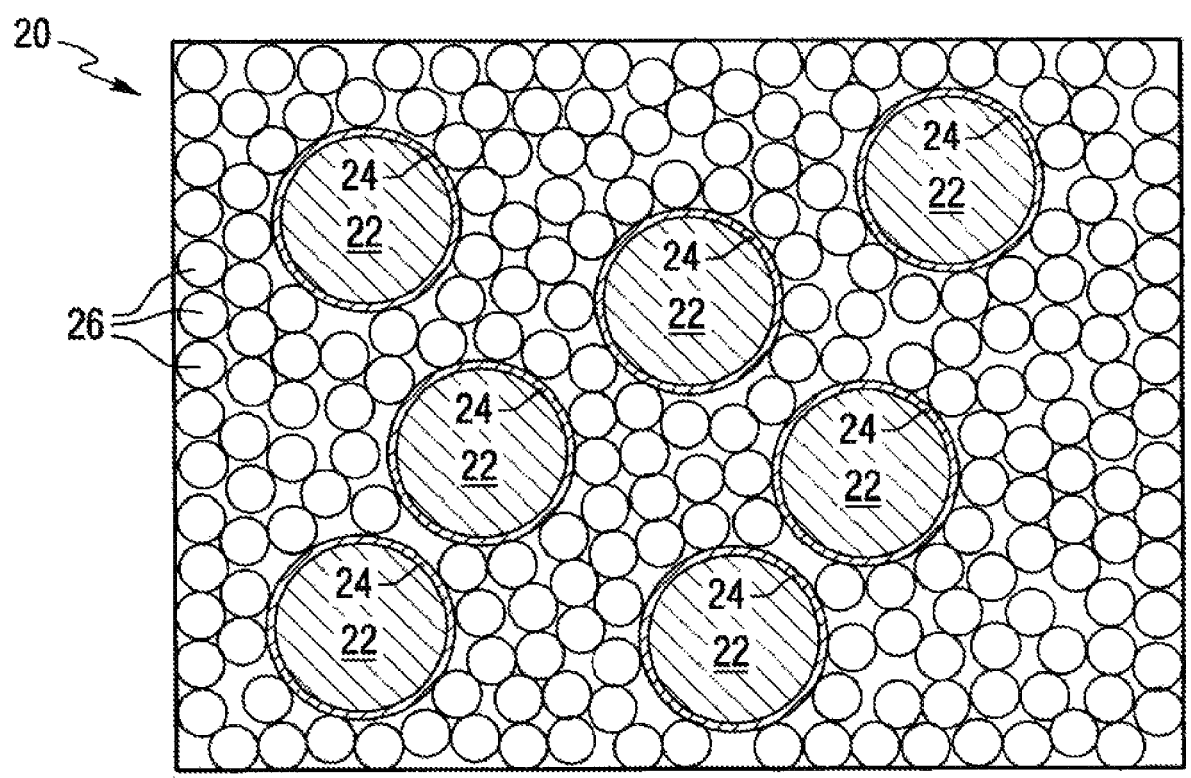
FIG. 2 is an illustration of a prenatal vitamin and aspirin compound dosage according to embodiments of the present disclosure.

FIG. 2 schematically illustrates a natal vitamin and aspirin compound dosage 20 in accordance with another embodiment of the present invention. In this embodiment, the aspirin is provided as several individual units 22, each of which includes a protective coating 24. The dosage 20 also includes vitamin and mineral constituents 26. In this embodiment, the number and weight of the aspirin units 22 are controlled in order to provide the desired amount of aspirin in the dosage. Although the dosage 20 shown in FIG. 2 comprises a loose powder mixture of the vitamin and mineral constituents 26, other forms may be used as noted previously.

Figure 3:
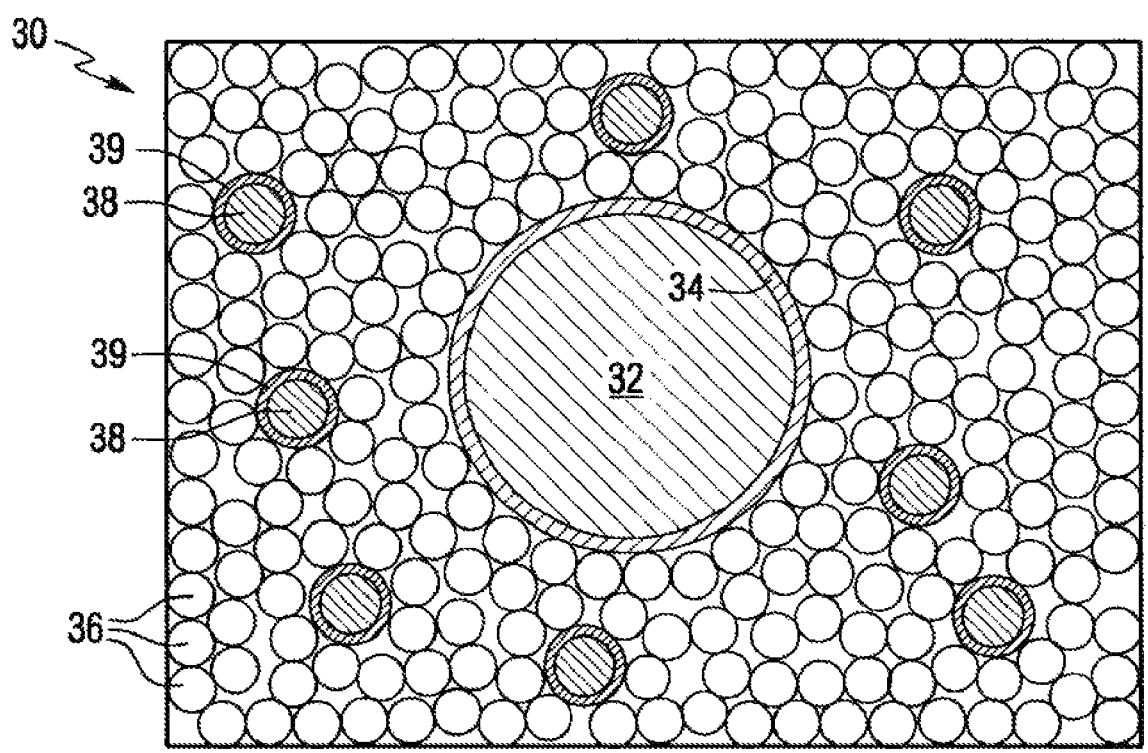
FIG. 3 is an illustration of a prenatal vitamin and aspirin compound dosage according to embodiments of the present disclosure.

FIG. 3 schematically illustrates a prenatal vitamin and aspirin compound dosage 30 in accordance with a further embodiment of the present invention. In this embodiment, the dosage 30 includes a single aspirin unit 32 having a protective coating 34. The dosage 30 may also include some or all of the vitamin and mineral constituents 36 in the preferred amounts listed previously. However, at least one of the vitamin and/or mineral constituents 38 may include a protective coating 39 that forms a barrier against unwanted reactions with the other vitamin and mineral constituents 36. The protective coating 39 may be the same as, or different from, the protective coating 34. As a particular example, the B vitamins, such as B12, may be provided with a protective coating in order to reduce or eliminate unwanted reactions with low pH ingredients such as ascorbic acid and aspirin. While both the aspirin 32 and vitamin/mineral constituent 38 are both provided with protective coatings in the embodiment shown in FIG. 3, the aspirin 32 may optionally be uncoated.

In accordance with some embodiments of the present disclosure, the compound dosage is stable and possesses extended shelf life. By providing a protective coating between the aspirin and the vitamin and mineral constituents, unwanted reactions which reduce shelf life are prevented or minimized. For example, without the protective coating, the aspirin may react with vitamin B12 and folate, thereby lowering the effective amounts of aspirin and these B vitamins contained in the dosage.

In addition to maintaining the effective amount of aspirin and vitamin and mineral constituents in the dosage, the use of a protective coating in accordance with the present invention may reduce or eliminate the formation of deleterious reaction products resulting from the unwanted interaction between the aspirin and the vitamin and mineral constituents.

The protective coating preferably extends the shelf life of the dosage to at least 365 days, more preferably to about 720 days. As used herein, the term "shelf life" means the maintenance of at least 90 percent of label potency for a specified time.

The above aspects of the present disclosure are meant to be illustrative. They were chosen to explain the principles and application of the disclosure and are not intended to be exhaustive or to limit the disclosure. Many modifications and variations of the disclosed aspects may be apparent to those of skill in the art. Persons having ordinary skill in the field of drug manufacturing and administering should recognize that components and process steps described herein may be interchangeable with other components or steps, or combinations of components or steps, and still achieve the benefits and advantages of the present disclosure. Moreover, it should be apparent to one skilled in the art, that the disclosure may be practiced without some or all of the specific details and steps disclosed herein. As used in this disclosure, the term "a" or "one" may include one or more items unless specifically stated otherwise. Further, the phrase "based on" is intended to mean "based at least in part on" unless specifically stated otherwise.

What is claimed is:

1. A compound dosage consisting of:
   one or more selected from the group of folic acid, vitamin D, calcium, vitamin C, thiamine, and riboflavin; and
   aspirin;
   wherein:
      the folic acid comprises from about 200 to about 600 micrograms;
      the vitamin D comprises from about 200 to about 600 international units;
      the calcium comprises from about 100 to about 400 milligrams;
      the vitamin C comprises from about 40 to about 100 milligrams;
      the thiamine comprises from about 1 to about 5 milligrams; and
      the riboflavin comprises from about 0.5 to about 3.5 milligrams.

2. The compound dosage of claim 1, wherein:
   the folic acid comprises from about 300 to about 500 micrograms;
   the vitamin D comprises from about 300 to about 500 international units;
   the calcium comprises from about 200 to about 300 milligrams;
   the vitamin C comprises from about 60 to about 80 milligrams;
   the thiamine comprises from about 2 to about 4 milligrams; and
   the riboflavin comprises from about 1 to about 2 milligrams.

3. A compound dosage consisting of:
   one or more selected from the group of folic acid, vitamin D, calcium, vitamin C, thiamine, and riboflavin;
   aspirin; and
   one or more selected from the group of niacin, vitamin B12, vitamin E, zinc, iron, omega 3 DHA, and iodine;
   wherein:
      the folic acid comprises from about 200 to about 600 micrograms;
      the vitamin D comprises from about 200 to about 600 international units;
      the calcium comprises from about 100 to about 400 milligrams;
      the vitamin C comprises from about 40 to about 100 milligrams;
      the thiamine comprises from about 1 to about 5 milligrams; and the riboflavin comprises from about 0.5 to about 3.5 milligrams.

4. The compound dosage of claim 3, wherein:
the niacin comprises from about 10 to about 30 milligrams;
the vitamin B12 comprises from about 2 to about 10 micrograms;
the vitamin E comprises from about 6 to about 14 milligrams;
the zinc comprises from about 10 to about 20 milligrams;
the iron comprises from about 13 to about 21 milligrams; and
the iodine comprises from about 100 to about 200 micrograms.

5. The compound dosage of claim 4, wherein:
the niacin comprises from about 15 to about 25 milligrams;
the vitamin B12 comprises from about 4 to about 8 micrograms;
the vitamin E comprises from about 8 to about 12 milligrams;
the zinc comprises from about 13 to about 17 milligrams;
the iron comprises from about 15 to about 19 milligrams; and
the iodine comprises from about 125 to about 175 micrograms.

6. A compound dosage consisting of:
one or more selected from the group of folic acid, vitamin D, calcium, vitamin C, thiamine, and riboflavin;
aspirin; and
one or more selected from the group of vitamin A, vitamin D3, vitamin E, vitamin K, folate, vitamin B1, vitamin B2, vitamin B3, vitamin B12, vitamin B6, magnesium, copper, inositol, boron, collagen, biotin USP, pantothenic acid, choline, calcium, iron, iodine, zinc, selenium, fish oil concentrate omega-3 fatty acids, DHA (docosahexanoic acid), EPA (eicosapentaenoic acid), para-aminobenzoic acid, vitamin K-2, chromium, manganese, sodium, molybdenum, potassium, and cholesterol;
wherein:
the folic acid comprises from about 200 to about 600 micrograms;
the vitamin D comprises from about 200 to about 600 international units:
the calcium comprises from about 100 to about 400 milligrams;
the vitamin C comprises from about 40 to about 100 milligrams;
the thiamine comprises from about 1 to about 5 milligrams;
the riboflavin comprises from about 0.5 to about 3.5 milligrams.

* * * * *